United States Patent
Stoeckel et al.

(10) Patent No.: US 9,534,995 B2
(45) Date of Patent: Jan. 3, 2017

(54) SYSTEM AND METHOD FOR DETERMINING A MODULUS OF RESILIENCE

(71) Applicant: Caterpillar Paving Products Inc., Brooklyn Park, MN (US)

(72) Inventors: Kristian Stoeckel, Plymouth, MN (US); Liqun Chi, Peoria, IL (US); Paul Corcoran, Washington, IL (US); Nicholas Oetken, Brooklyn Park, MN (US)

(73) Assignee: Caterpillar Paving Products Inc., Brooklyn Park, MN (US)

( * ) Notice: Subject to any disclaimer, the term of this patent is extended or adjusted under 35 U.S.C. 154(b) by 29 days.

(21) Appl. No.: 14/301,778

(22) Filed: Jun. 11, 2014

(65) Prior Publication Data

US 2015/0362414 A1    Dec. 17, 2015

(51) Int. Cl.
*G01N 3/08* (2006.01)
*E02D 3/02* (2006.01)
*E02D 1/02* (2006.01)
*G01N 33/24* (2006.01)
*E02D 3/026* (2006.01)

(52) U.S. Cl.
CPC ............... *G01N 3/08* (2013.01); *E02D 1/022* (2013.01); *E02D 3/026* (2013.01); *G01N 33/24* (2013.01); *G01N 2203/0019* (2013.01); *G01N 2203/0085* (2013.01)

(58) Field of Classification Search
CPC ...... E01C 19/235; E01C 19/288; E02D 3/026; E02D 3/0265; E02D 1/022; G01N 3/08; G01N 33/24; G01N 2203/0019; G01N 2203/0085

See application file for complete search history.

(56) References Cited

U.S. PATENT DOCUMENTS

| | | | |
|---|---|---|---|
| 5,727,900 A * | 3/1998 | Sandstrom | G01P 15/18 404/122 |
| 5,797,699 A * | 8/1998 | Blancke | E01C 19/288 404/117 |
| 6,065,904 A | 5/2000 | Cook et al. | |
| 6,188,942 B1 * | 2/2001 | Corcoran | E01C 19/006 701/408 |
| 6,244,102 B1 * | 6/2001 | Novak | E01C 19/288 73/594 |
| 7,873,492 B2 * | 1/2011 | Ackermann | E01C 19/288 702/150 |
| 7,938,595 B2 * | 5/2011 | Potts | E01C 19/288 404/84.1 |

(Continued)

FOREIGN PATENT DOCUMENTS

| | | |
|---|---|---|
| CN | 200959012 Y | 10/2007 |
| CN | 101205715 A | 6/2008 |
| CN | 102879286 A | 1/2013 |

*Primary Examiner* — Abigail A Risic
(74) *Attorney, Agent, or Firm* — Baker & Hostetler LLP

(57) ABSTRACT

A system for determining a modulus of resilience of a work material during a compaction operation includes a processor configured to determine a work material stiffness based on a force applied to the work material and a displacement of the work material, and determine the modulus of resilience of the work material based on a relationship between the work material stiffness and the modulus of resilience of the work material.

17 Claims, 6 Drawing Sheets

(56) References Cited

U.S. PATENT DOCUMENTS

| | | | | |
|---|---|---|---|---|
| 8,190,338 B2* | 5/2012 | Commuri | ............. | E01C 19/288 |
| | | | | 701/50 |
| 8,439,598 B2* | 5/2013 | Norton | .................... | E01C 19/26 |
| | | | | 404/75 |
| 2004/0035207 A1* | 2/2004 | Hamblen | .................. | E02D 1/02 |
| | | | | 73/573 |
| 2007/0150147 A1* | 6/2007 | Rasmussen | ........... | E01C 19/004 |
| | | | | 701/50 |
| 2007/0276602 A1* | 11/2007 | Anderegg | ............. | E01C 19/288 |
| | | | | 702/2 |
| 2013/0261998 A1* | 10/2013 | Anderegg | ................ | G01N 3/32 |
| | | | | 702/56 |

\* cited by examiner

SYSTEM AND METHOD FOR DETERMINING A MODULUS OF RESILIENCE

TECHNICAL FIELD

This disclosure relates generally to machines that compact material, and more particularly, to a system and method for determining a modulus of resilience of soil during the soil compaction process.

BACKGROUND

Compacting machines or compactors are commonly used to compact work materials (such as soil, gravel, asphalt) to a desired density while constructing buildings, highways, parking lots, and other structures. Often, earthen material at a worksite must be compacted and one or more compacting machines must be involved to successively compact material until the desired level of compaction is achieved. The process may require many passes over the work material to reach the desired level. A modulus of resilience is one measurement used to determine the level of compaction.

There are a variety of methods for determining a modulus of resilience of a soil or other material. Current technology includes the use of nuclear density gauges, plate load testing deflectometers, or the like, that measure soil density or soil stiffness either before and/or after a compaction process. Although this may provide an accurate measurement for the compaction of the soil or other material, these measures must be performed separately from the compaction process. Systems for measuring compaction during the compaction process are known. U.S. Pat. No. 8,057,124 B2, assigned to Wacker Neuson Produktion GmbH & Co., discloses a method and device for measuring soil parameters. It uses an approximation of the actual gradient of the contact force and a contact surface parameter to calculate a dynamic modulus of deformation. However, this modulus is dimensionless.

Current methods fail to provide a modulus of resilience with an engineering unit value that can be determined during the compaction process. A disadvantage for current methods is that a unitless modulus of resilience cannot be used for other purposes, such as by a design engineer who needs to know the specific compaction of the soil or other material in order to build or design roads, building pads, etc. The present disclosure is directed to overcoming or mitigating one or more of these problems set forth.

The foregoing background discussion is intended solely to aid the reader. It is not intended to limit the innovations described herein, nor to limit or expand the prior art discussed. Thus, the foregoing discussion should not be taken to indicate that any particular element of a prior system is unsuitable for use with the innovations described herein, nor is it intended to indicate that any element is essential in implementing the innovations described herein. The implementations and application of the innovations described herein are defined by the appended claims.

SUMMARY

An embodiment of the present disclosure includes a method and system for determining a modulus of resilience of a work material being compacted by a compactor system having a roller drum. The disclosed method includes sensing or calculating, with at least one sensor and/or a processor, a contact force applied on the work material by the roller drum and a vertical displacement of the roller drum. The method further includes calculating a work material stiffness with the processor based on the contact force and the vertical displacement. The modulus of resilience of the work material is determined by the processor based on a relationship between the work material stiffness and the modulus of resilience of the work material.

Another embodiment of the present disclosure includes a compactor system for determining a modulus of resilience of a work material during a compaction operation. The compactor system includes at least one roller drum, at least one sensor, and a processor. The at least one roller drum is configured to compact the work material. The at least one sensor is configured to sense at least one of a vertical acceleration, vertical displacement, and a force of a compactor system component. The processor is configured to calculate a contact force at an interface between the at least one roller drum and the work material in response to the at least one sensor, a displacement of the at least one roller drum in response to the at least one sensor, and to calculate the stiffness of the work material based on the contact force and the displacement. The processor is further configured to determine the modulus of resilience of the work material based on a relationship between the work material stiffness and the modulus of resilience of the work material.

Another embodiment of the present disclosure includes a compactor system having a processor for determining a modulus of resilience of a work material during a compaction operation. The processor is configured to determine a work material stiffness based on a force applied to the work material by the compactor system and a vertical displacement of the compactor system. The processor is further configured to determine the modulus of resilience of the work material based on a relationship between the work material stiffness and the modulus of resilience of the work material.

DETAILED DESCRIPTION OF ILLUSTRATIVE EMBODIMENTS

The disclosure relates generally to a system and method for determining a modulus of resilience of a work material having engineering units while the work material is being compacted by a compactor or machine. The method includes having loose material disposed over a surface, which can be further packed or densified. A compactor or machine travels over the surface of the diposed material, generating forces acting in cooperation with the weight of the machine, which are imparted onto the material compressing it to a state of greater stiffness and density. The compactor may make one or more passes over the surface to provide a desired level of work material compaction. The material being compacted may include asphalt, soil, gravel, sand, land fill trash, concrete, or the like. Hereinafter the material being compacted may be referred to as the work material.

Figure 1:
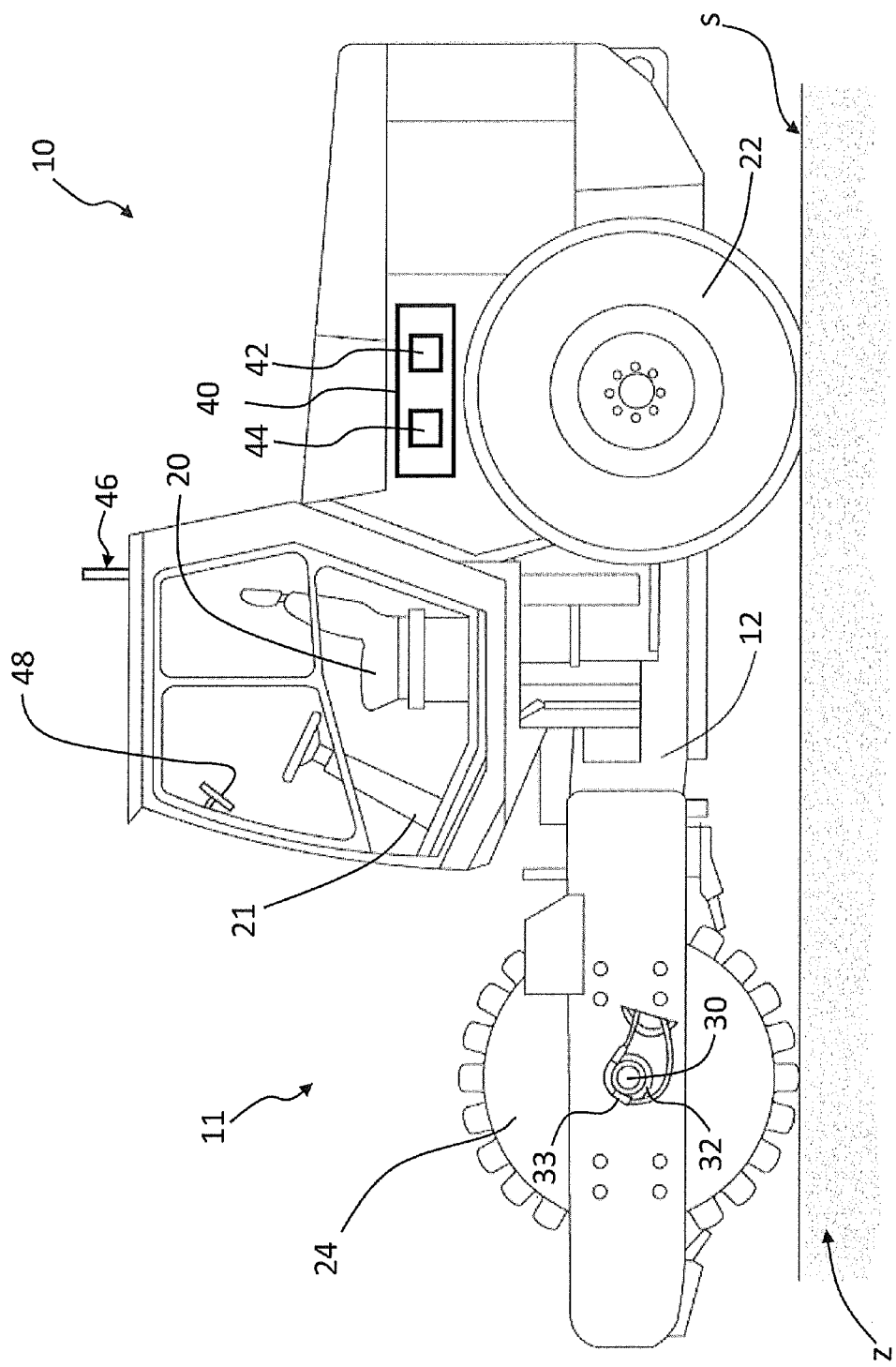
FIG. 1 is a side view of a compactor system, according to one aspect of the disclosure.

FIG. 1 illustrates the side view of a compactor system, according to one aspect of the disclosure. In this view, an exemplary compactor system 10 is shown that can travel over a surface S compacting a work material Z under its own power and may implement aspects of the disclosure. Other types of compactors are contemplated to implement the disclosed process and device including soil compactors, asphalt compactors, utility compactors, pneumatic compactors, vibratory compactors, self-propelled two-wheel and four-wheel compactors, and tow-behind systems. The compactor system 10 includes a compactor machine 11 that includes a body or frame 12 that inter-operatively connects and associates the various physical and structural features that enable the compactor machine 11 to function. These features may include an operator cab 20 that is mounted on top of the frame 12 from which an operator may control and direct operation of the compactor machine 11. Additionally, a steering feature 21 and similar controls may be located within the operator cab 20. To propel the compactor machine 11 over the surface S, a power system (not shown), such as an internal combustion engine, can also be mounted to the frame 12 and can generate power that is converted to physically move the compactor machine 11. One or more other implements (not shown) may be connected to the machine. Such implements may be utilized for a variety of tasks, including, for example, loading, lifting, and brushing, and may include, for example, buckets, forked lifting devices, brushes, grapples, cutters, shears, blades, breakers/hammers, augers, and others.

To enable physical motion of the compactor machine 11, the illustrated compactor machine 11 includes a padfoot drum 24 and rubber tires 22 that are in rolling contact with the surface S. It should be appreciated that machine 11 may have two roller drums for compacting the work material Z, and the drums (or drum in the case of a single drum compactor) may be smooth or equipped with compacting feet, such as a padfoot type design. For reference purposes, the compactor machine 11 can have a typical direction of travel such that the padfoot drum 24 may be considered the forward drum and the rubber tires 22 considered the rear of the machine 10. The padfoot (forward) drum 24 and rubber tires (rearward) 22 can be cylindrical structures that are rotatably coupled to and can rotate with respect to the frame 12. Because of their forward and rearward positions and their dimensions, the padfoot drum (forward) 24 and rubber tires (rearward) 22 support the frame 12 of the compactor machine 11 above the surface S and allow it to travel over the surface S. The padfoot drum (forward) 24 and rubber tires (rearward) 22 are oriented generally transverse or perpendicular to the direction of travel of the compactor machine 11. It should be appreciated that because the compactor machine 11 is steerable, the forward direction of travel may change bearing during the course of operation but can be typically assessed by reference to the direction of movement of the padfoot drum (forward) 24. In the illustrated aspect, to transfer motive power from the power system to the surface S, the power system can operatively engage and rotate the rubber tires (rearward) 22 through an appropriate power train.

Figure 2:
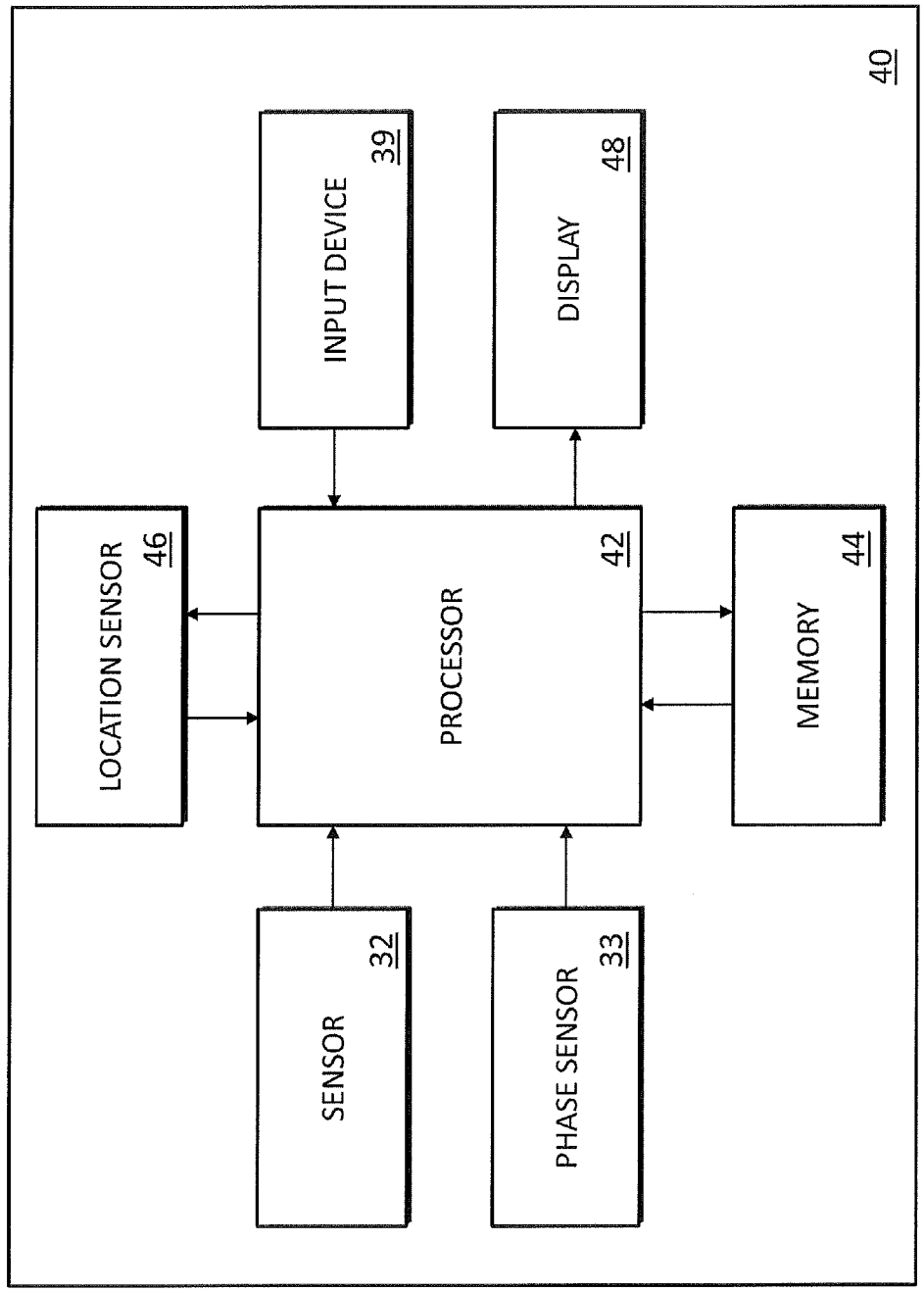
FIG. 2 is an illustration of a block diagram of an embodiment of a controller.

To facilitate control and coordination of the compactor machine 11, the compactor machine 11 may include a controller 40 such as an electronic control unit. While the controller 40 illustrated in FIG. 1 is represented as a single unit, in other aspects the controller 40 may be distributed as a plurality of distinct but interoperating units, incorporated into another component, or located at a different location on or off the compactor machine 11. FIG. 2 illustrates a block diagram of an embodiment of the components that may comprise the controller 40. The controller 40 may include a sensor 32, a phase sensor 33, an input device 39, a processor 42, a memory 44, a location sensor 46, a display or output 48, and a vibration system (not shown). The main unit of the controller 40 may be located in the operator cab 20 for access by the operator and may communicate with the steering feature 21, the power system, and with various other sensors and controls on the compactor machine 11.

A machine or compactor having a controller is described in U.S. patent application Ser. No. 14/163,900, the content of which is incorporated herein by reference ("the '900 application"). The controller uses values sensed by a sensor, which may be stored in the memory, for soil compaction calculations using an algorithm stored in memory. Thus, an embodiment of compactor machine 11 may include a controller configuration as disclosed by the '900 application.

The sensor 32 may be configured to sense a parameter indicative of the acceleration, velocity, displacement, and/or force of a component of the compactor machine 11. The components may include the padfoot drum (forward) 24, the rubber tires (rearward) 22, a roller drum (not shown), the compactor frame 12, or the like. Sensor 32 may include a signal transducer configured to sense a transmitted signal, or component of a transmitted signal. For example, the signal reflected by surface S. As illustrated in FIG. 1, a single sensor 32 is shown coupled with and resident on padfoot drum (forward) 22. In other aspects, additional sensors such as a rearward sensor (not shown) associated with rubber tires (rearward) 22 or a rear roller drum, individual sensors located in proximity to the padfoot drum (forward) 24 and/or rubber tires (rearward) 22, or separate sensors for measuring acceleration and/or displacement of the padfoot drum (forward) 24, the rubber tires (rearward) 22, a roller drum, and the compactor frame 12 may be used.

In another embodiment, sensor 32 may comprise several different sensors. One sensor 32 may sense the vertical acceleration of the padfoot drum (forward) 24 and/or rubber tires (rearward) 22 and a second sensor 32 may detect the vertical acceleration of the compactor frame 12. These sensors 32 may be located proximate to each other but they need not be. Additionally, there may be more than one of each type of sensor 32 located on the compactor machine 11. For example, there may be a sensor 32 sensing the vertical acceleration of the padfoot (forward) drum 24 and a second sensor 32 sensing the vertical acceleration of the rubber tires (rearward) 22 or rear roller drum. While the acceleration of the drum 24, rubber tires 22, and the compactor frame 12 may be used, the drum acceleration only may be used as the primary signal. The accelerometer used can be any type of accelerometer. Such accelerometers include, but are not limited to, laser accelerometers, low frequency accelerometers, bulk micromachined capacitive accelerometers, strain gauge accelerometers, and bulk micromachined piezoelectric accelerometers among others.

In an embodiment, the sensor 32 may sense force. In this case, the sensor 32 may be, but is not limited to, a load cell, a strain gauge, or the like.

In an embodiment, the sensor 32 may be located at or close to the axle 30. In another embodiment, the sensor 32 may be located at or close to the center of frame 12. The transmitted signal may include a sonic signal, an RF signal, or a laser signal, for example, transmitted via a transmitter (not shown) mounted with sensor 32. Sensor 32 may include a non-contact sensor such as examples noted above.

The compactor machine 11 may also include a phase sensor 33 and a location sensor 46. The phase sensor 33 may be configured to measure the phase angle of a vibratory force imparted by the padfoot drum (forward) 24, the rubber tires (rearward) 22, and/or a roller drum (not shown) to the ground. The phase may be measured in real time. The location sensor 46, resident on compactor machine 11, may be configured to receive global or local positioning data used in establishing and tracking geographic position of compactor machine 11 within a work area.

The compactor machine 11 may also include a vibratory or vibration system (not shown) associated with the padfoot drum (forward) 24, rubber tires (rearward) 22, and/or a roller drum to impart a compacting force onto the work material Z. More specifically, in addition to the force of the compactor machine 11 being applied to the work material Z to apply compressive forces, the vibration system within the padfoot drum (forward) 24, the rubber tires (rearward) 22, and/or a roller drum may operate to apply additional forces to the work material Z. The vibration system may include any type of system that imparts vibrations, oscillations, or other repeating forces through the padfoot drum (forward) 24, the rubber tires (rearward) 22, and/or a roller drum onto the work material Z.

As illustrated in FIG. 2, the data processor 42 may be coupled to the sensor 32, phase sensor 33, and the location sensor 46. The data processor 42 may be configured to output signals that are responsive to inputs from sensor 32, as further described herein. A display 48 may also be coupled with the processor 42 and may be positioned in the operator cab 20 to display various data to an operator relating to the machine position, ground stiffness, modulus of resilience, or still other parameters. Action may be taken in response to the modulus of resilience or other compaction metrics including commencing the compaction process within the work area, stopping travel of the compactor machine 11, or redirecting or otherwise changing a planned compactor travel path or coverage pattern.

The processor 42 utilizes the values sensed by the sensor 32 that may be stored in computer readable memory 44 to determine a modulus of resilience value using algorithms stored in the memory 44. The processor 42 may compare the determined modulus of resilience to a predetermined minimum modulus of resilience value that may have been input by an input device 39. If the determined modulus of resilience meets or exceeds the minimum modulus of resilience value, the processor 42 may send a signal to the display 48 communicating that the work material Z has been sufficiently compacted. If the modulus of resilience value does not meet or exceed the minimum modulus of resilience value, then the processor 42 may send a signal to the display 48 communicating that further compaction is required. Examples of processors include computing devices and/or dedicated hardware as defined herein, but not limited to, one or more central processing units and microprocessors.

The computer readable memory 44 may include random access memory (RAM) and/or read-only memory (ROM). The memory 44 may store computer executable code including a control algorithm for determining a modulus of resilience value of work material Z responsive to inputs from sensor 32. The memory 44 may also store various digital files including the values sensed by sensor 32, phase sensor 33, or location sensor 46. The memory 44 may also store information input from the input device 39. The information stored in the memory 44 may be provided to the processor 42 so that the processor may determine a modulus of resilience.

The display 48 may be located either on the compactor machine 11, located remotely, or may include multiple displays both on the machine and remotely, and may include, but not limited to, cathode ray tubes (CRT), light-emitting diode display (LED), liquid crystal display (LCD), organic light-emitting diode display (OLED) or a plasma display panel (PDP). Such displays can also be a touch-screen and may incorporate aspects of the input device 39. The display 48 may also include a transceiver. The transceiver communicates over a communication channel as defined herein.

Figure 3:
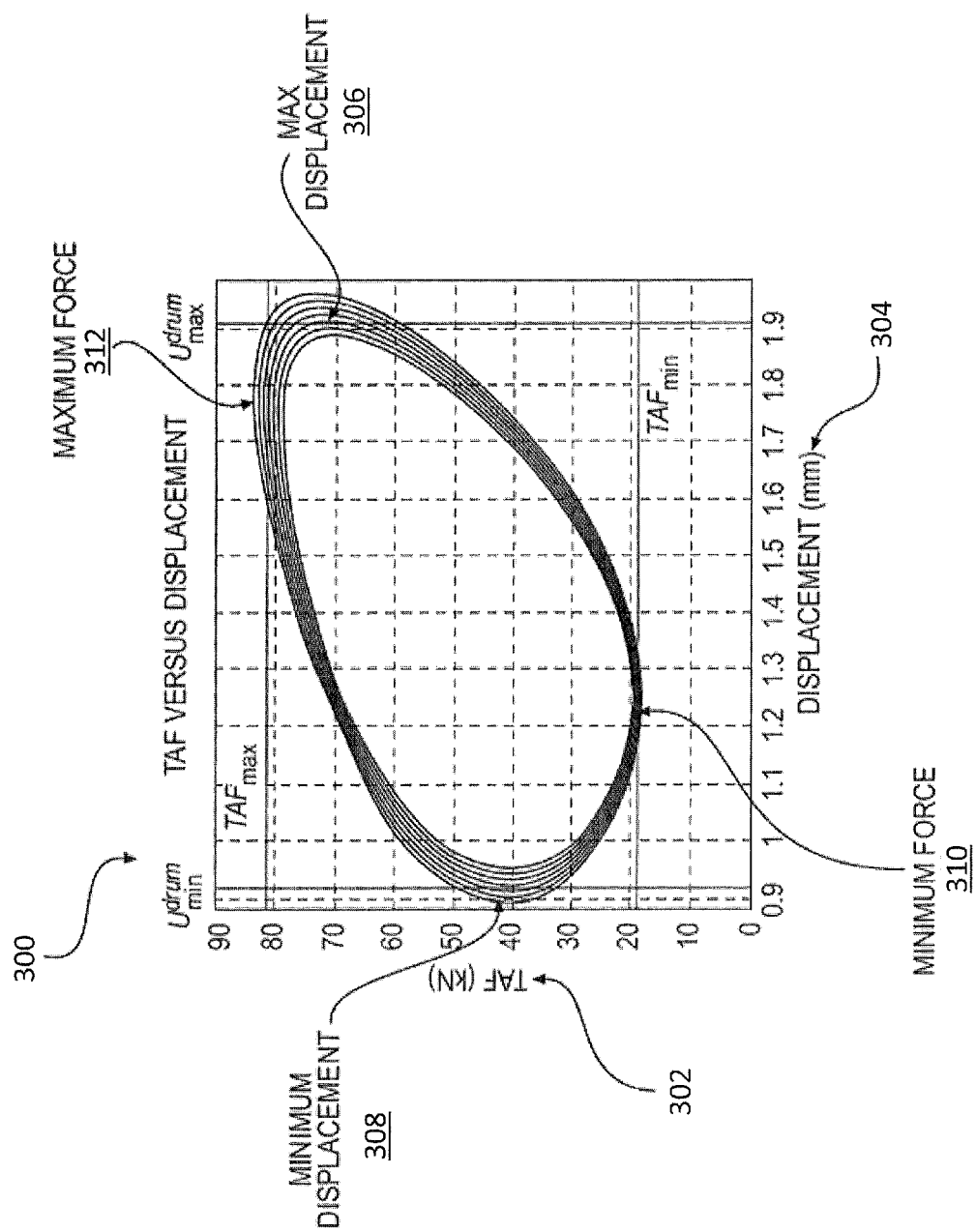
FIG. 3 is a graph depicting the contact force between a drum and the ground during downward compaction and upward retraction according to one aspect of the disclosure.

FIG. 3 is a graph 300 depicting the contact force between the padfoot drum (forward) 24, the rubber tires (rearward) 22, and/or a roller drum and the ground S during downward compaction and upward retraction according to one aspect of the disclosure. In particular, FIG. 3 is a graph showing the total applied force (TAF) that the padfoot drum (forward) 24, rubber tires (rearward) 22, and/or a roller drum, and the compactor frame 12 apply to the ground S compared to the displacement of the padfoot drum (forward) 24, the rubber tires (rearward) 22, and/or a roller drum. In particular, this graph 300 shows multiple cycles of drum operation 302, 304. Starting at the minimum displacement 308, the TAF is roughly 40 kN and the displacement is roughly 0.9 mm, and tracing the graph to the maximum displacement 306, where the TAF is roughly 75 kN and the displacement is roughly 1.9 mm, represents the loading portion of the compaction process. Starting at the point of maximum displacement 306, and continuing to the left to the point of minimum force 310, represents the unloading portion of the compaction process. The displacement between the minimum force 310 and the minimum displacement 308 is considered the rebound of the ground S. It should be noted that the values in FIG. 3 and described hereinabove are merely exemplary.

Figure 4B:
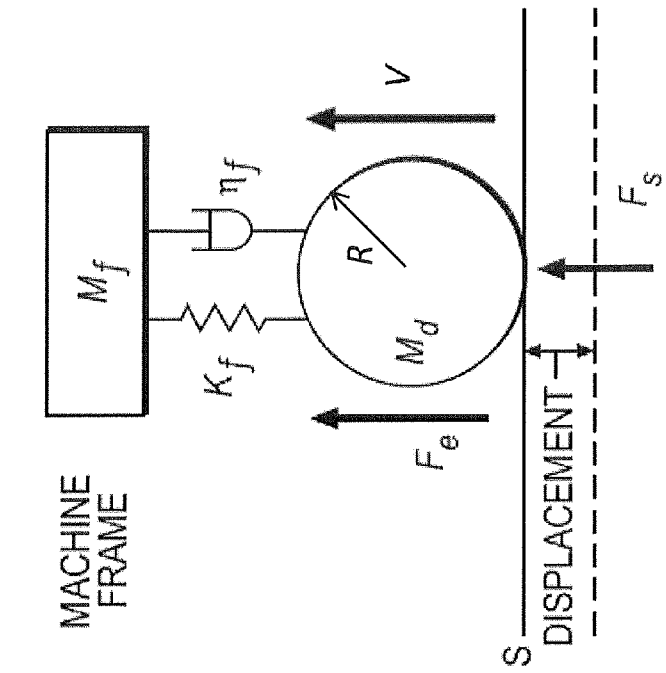
FIGS. 4A and 4B are free body diagrams depicting the various forces and movements while compacting in one aspect of the disclosure.
Figure 4A:
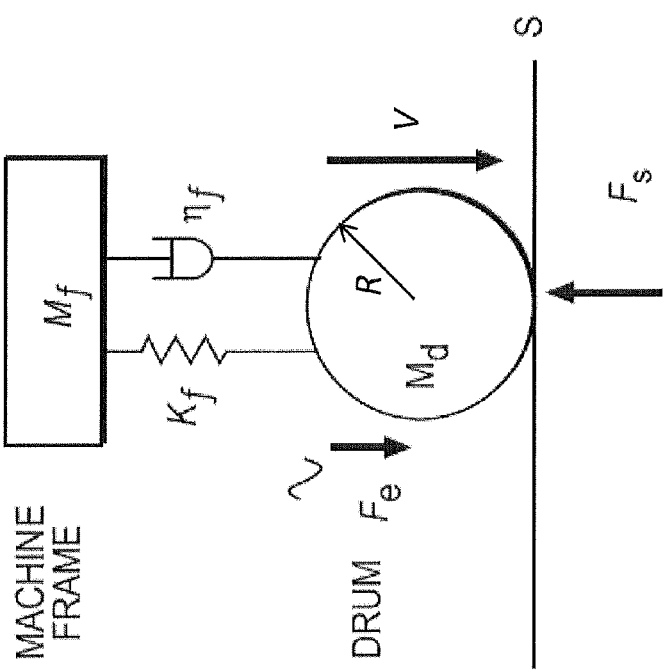
Figure 5:
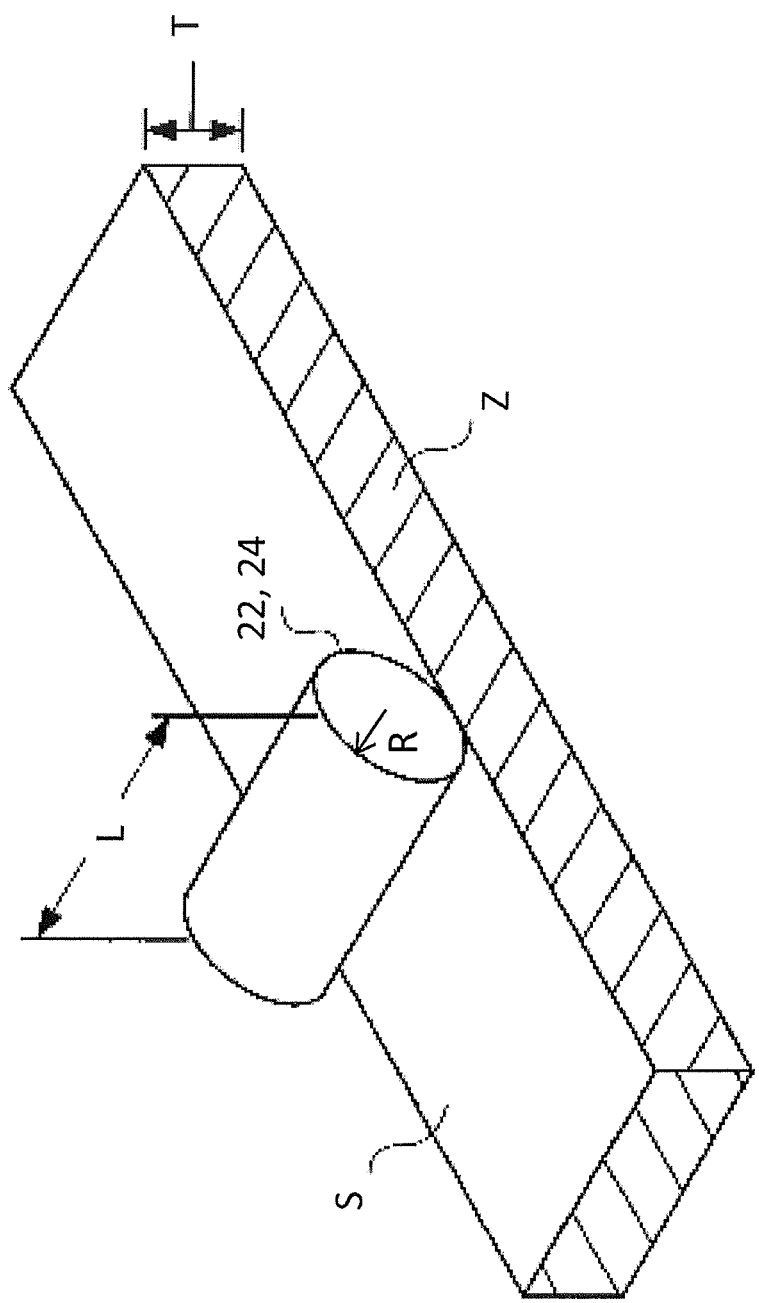
FIG. 5 is an illustration of a roller drum on a portion of work material to be compacted.

FIGS. 4A and 4B show free body diagrams illustrating the mechanical components and the Newtonian forces present while the compactor system 10 compacts the surface of a work area. A portion of the compactor frame 12 mass $M_f$ and the mass of a drum, either the padfoot drum (forward) 24 or roller drum (not shown), $M_d$, together with their respective accelerations, combine to form a downward force, $F_e$, on the surface S in order to further compact the surface S. The padfoot drum (forward) 24 and/or roller drum have a radius, R, and a length or width, L (FIG. 5). The ground reaction force is represented by $F_s$. The Spring-Damper System, $K_f$ and $\eta_f$, represent the damping mechanism properties of the compactor machine 11. FIG. 4A represents the compactor system 10 when it is loading, or compressing, the ground. Loading may be defined by a drum downward motion with increasing contact force. This is illustrated by the downward pointing force $F_e$. FIG. 4B represents the compactor system 10 when it is unloading from the ground. Unloading may be defined as a roller drum upward motion with decreasing contact force. This is illustrated by the upward pointing force $F_e$. The displacement is the difference in the padfoot drum (forward) 24 and/or roller drum height when the padfoot drum (forward) 24 and/or roller drum is compressing the ground and the padfoot drum (forward) 24 and/or roller drum height when the padfoot drum (forward) 24 and/or roller drum is not compressing the ground.

FIG. 5 is a diagrammatic illustration of a cross-section of a volume of the work material Z and either the padfoot (forward) drum 24 or a roller drum having a length or width, L, and radius, R. The work material Z has a thickness T, which may decrease during the compaction process.

Figure 6:
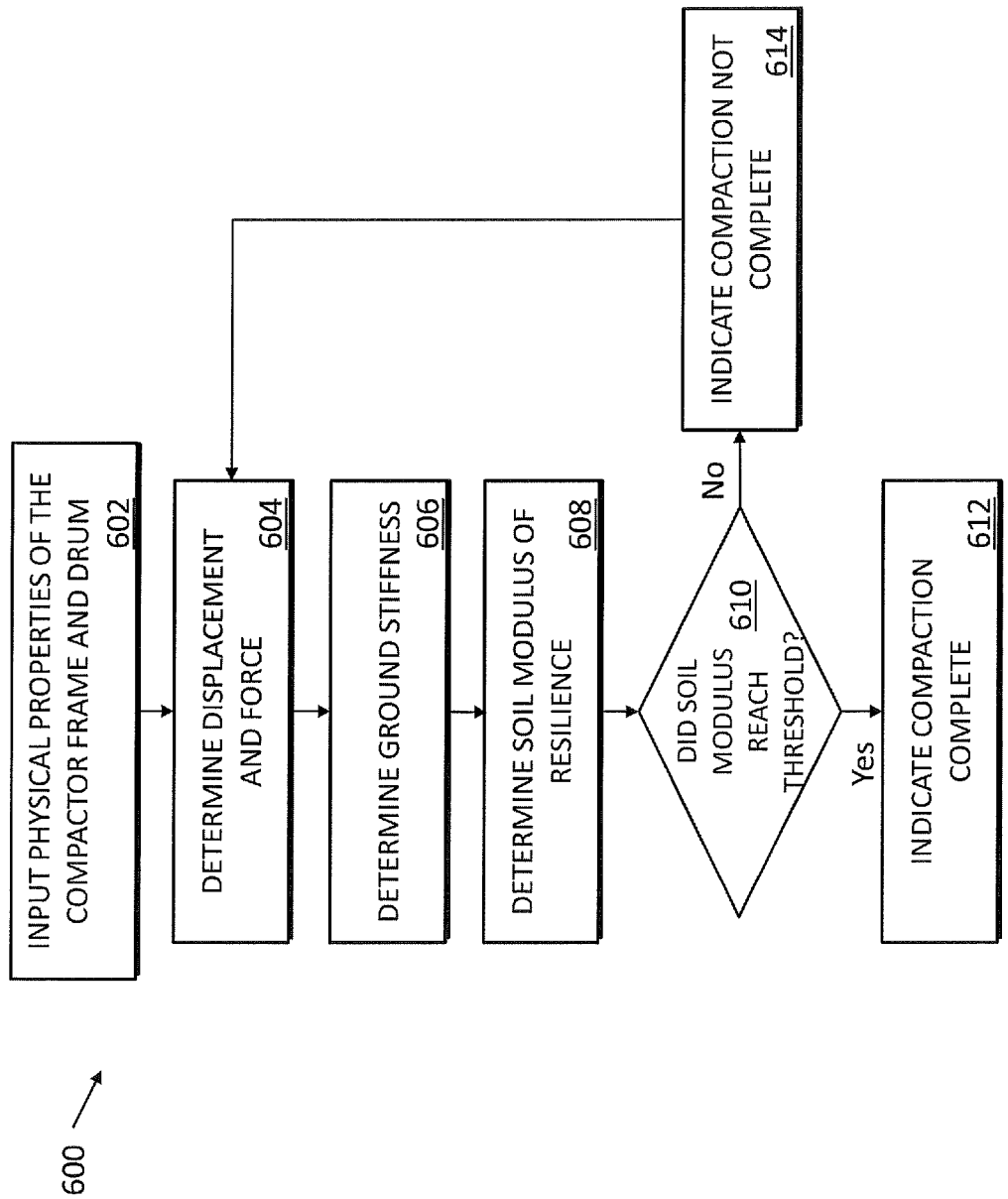
FIG. 6 is a flowchart depicting a method of determining a modulus of resilience of a work material.

FIG. 6 is a flowchart depicting a method for determining the modulus of resilience of a work material undergoing compaction using the disclosed system, according to an embodiment of this disclosure. During the compaction process, the processor 42 may be configured to determine the real-time or near real-time contact force at the drum-ground interface and the drum displacement. Using these values the ground stiffness may be calculated and used in the determination of a real-time or near real-time modulus of resilience of the work material.

In step 602, the physical properties of the compactor frame 12, the padfoot drum (forward) 24, and/or a roller drum (not shown) are determined. In an embodiment, this may be performed prior to the compaction operation. The physical properties may include the mass of the padfoot drum (forward) 24 and/or roller drum, the mass of the compactor frame 12 exerted on the padfoot drum (forward) 24 and/or roller drum, the radius and length or width of the padfoot drum (forward) 24 and/or roller drum, and the like. These properties may be constant for a particular compactor machine. They may be input manually to memory 44 from an input device 39, or selected from a database of pre-stored values stored in memory 44.

In 604, a contact force at an interface between the roller drum and the work material is calculated using the physical properties determined from step 602, the vertical acceleration of the padfoot drum (forward) 24 and/or roller drum, and the vertical acceleration of the compactor frame 12, and the vibrational properties, if any, of the padfoot drum (forward) 24 and/or roller drum. The contact force may also be determined by using the sensor 32, which may include direct sensing such as a force sensor. The sensor 32 may also sense the vertical accelerations of the roller drums 24, 22 and the compactor frame 12, and the vibrational properties. In an embodiment, the sensor 32 may be an accelerometer. An equation that may be used to calculate the contact force at the roller drum-work material interface is as follows:

$$F_s = (M_d + M_f)g - M_d \ddot{x}_d - M_f \ddot{x}_f + F_e \sin(\omega_0 t + \phi_0) \quad \text{Equation 1:}$$

where $F_s$ is the contact force, $M_d$ is the unsprung mass of the padfoot drum (forward) 24 and/or roller drum, $M_f$ is the equivalent frame mass on the drum axle, $\ddot{x}_d$ is the vertical acceleration of the padfoot drum (forward) 24 and/or roller drum, $\ddot{x}_f$ is the vertical acceleration of the frame, $F_e$ is the amplitude of the vibratory force, $\omega_0$ is the angular frequency of the vibratory force, and $\phi_0$ is the phase angle of the vibratory force.

The padfoot drum (forward) 24 and roller drum displacement can be calculated by using the drum acceleration values that the sensor 32 has sensed. To calculate a displacement value from an acceleration value, the acceleration value may be integrated twice. In other words, the displacement value can be calculated according to the following formula:

$$x = x_0 + \int_0^t [\dot{x}_0 + \int_0^t \ddot{x}_0] dt \quad \text{Equation 2:}$$

where x is the displacement of the padfoot drum 24 and/or roller drum, $x_0$ is the initial vertical displacement of the padfoot drum (forward) 24 and/or roller drum at the beginning of each sample cycle, $\dot{x}_0$ is the initial vertical velocity of the padfoot drum (forward) 24 and/or roller drum at the beginning of each sampling cycle, and $\ddot{x}_0$ is the vertical acceleration of the padfoot drum (forward) 24 and/or roller drum. The initial displacement $x_0$ does not affect the energy and stiffness calculation so, as a simplification, it can be set to zero. However, the initial vertical velocity $\dot{x}_0$ will affect the energy and stiffness calculations. An initial vertical drum velocity $\dot{x}_0$ is determined by making zero average velocity during a complete sampling cycle, which is normally two or more vibratory cycles. When compacting level ground, the average vertical velocity of the padfoot drum (forward) 24 and/or roller drum is almost zero. However, when compacting on a slope, the average vertical velocity is not zero. Setting the average vertical velocity to zero will remove the effect created by the slope. Other approaches to determine x are contemplated, including a sensor 32 implemented as a distance sensor.

Once the contact force at the drum-ground interface and the displacement of the padfoot drum (forward) 24 and/or roller drum is calculated, the ground stiffness value can be calculated at 606. To calculate the ground stiffness value, the information needed is the maximum and the minimum TAF and the maximum and the minimum roller drum displacement values. The ground stiffness value can be calculated according to the following equation:

$$k_{dyn} = \text{mean}\left[\frac{(TAF_{max} - TAF_{min})}{u_{max}^{drum} - u_{min}^{drum}}\right] \quad \text{Equation 3}$$

where the unit of the calculation is force per length, which aligns with the stiffness measure. It should be appreciated that other calculations may be used to calculate a ground stiffness value.

In step 608, the ground stiffness determined in step 606 may be used in determining a work material modulus of resilience. The modulus of resilience of a work material is the physical property of the work material condition related to the ability of the work material to support a load. The modulus of a work material may be determined by relating the modulus to the ground stiffness property. The following equation is an embodiment of this relationship:

$$k_{dyn} = \frac{E \cdot L \cdot \pi}{2 \cdot (1 - v^2) \cdot \left(2.14 + \frac{1}{2} \cdot \ln\left[\frac{\pi \cdot L^3 \cdot E}{(1 - v^2) \cdot 16 \cdot (M_f + M_d) \cdot R \cdot g}\right]\right)} \quad \text{Equation 4}$$

where $k_{dyn}$ is the previously calculated ground stiffness value from Equation 3, having units of force per length. This equation illustrates an embodiment of the relationship between the ground stiffness and the modulus of resilience. It should be appreciated that other equations or relationships relating ground stiffness and modulus of resilience may be used.

In Equation 4, v is Poisson's ratio of the work material being compacted, L is the length or width of the padfoot drum (forward) 24 and/or roller drum, $M_d$ is the unspring mass of the padfoot drum (forward) 24 and/or roller drum, $M_f$ is the equivalent frame mass on the drum axle, R is the radius of the padfoot drum (forward) 24 and/or roller drum, E represents the modulus of resilience of the work material, and the constant g represents gravitational acceleration. As with determining the contact force, $F_s$, from Equation 1, the physical properties, as determined during step 602, of the compactor machine 11 are needed. In addition to the frame mass, $M_f$, and the unsprung mass of the padfoot drum (forward) 24 and/or roller drum, $M_d$, the dimensions of the length or width, L, and the radius, R, of the padfoot drum (forward) 24 and/or roller drum are used for determining the modulus, E. The resulting modulus, E, will have units of force per area. Additionally, a physical property of the work material is needed, which includes Poisson's ratio, v. The Poisson's ratio is the ratio of transverse to axial strain of the work material and it will vary depending on the work material being compacted. For commonly used work materials, the range of Poisson's ratios may be between 0.20 and 0.50. The volume of the material may only decrease slightly during compaction for materials at the higher end of this range (e.g. saturated clay). For materials at the lower end of the range (e.g. concrete, sand, clay) the change in volume may be more apparent. It should be appreciated that this range of ratios is merely exemplary and this disclosure may apply to materials with Poisson ratios outside this range.

In determining the modulus of resilience, E, the processor 42 may be configured to use an iterative method to solve Equation 4. This may include a mathematical procedure that generates a sequence of improving approximate solutions for a given equation. Preconditioners may be used, such as an initial modulus value, for instance, the modulus of the previous compactor pass, which may help increase the rate of convergence.

The determination of the modulus of resilience, E, may be performed during the compaction process by the processor 42. Once the modulus of resilience is determined, at step 610, the processor 42 may compare the value to a predetermined threshold modulus of resilience for the work area being compacted. The threshold value may be a value input by a user via an input device 39 or a stored value. At 614, if the modulus is below the threshold, the processor 42 may send a signal to the display 48 to indicate that further compaction is required. The operator may compact the work material further by performing more passes until the determined modulus of resilience reaches the threshold value. The process steps 604, 606, 608, and 610 are then repeated for each continuing compactor pass. Once the modulus of resilience meets the threshold modulus of resilience required for the work area, then the processor 42 may send a signal to the display 48 that no further compaction is needed and the process ends at 612.

INDUSTRIAL APPLICABILITY

The present disclosure provides an advantageous system and method for determining the modulus of resilience of a work material during a compaction process. The system uses the physical characteristics of the compactor machine and the work material in conjunction with force and acceleration of the roller drum and frame to accurately and efficiently determine a real-time or near real-time modulus of resilience. Instead of requiring a multiple step process for compacting a work material and measuring the resilience, this system synthesizes the compaction and determination of the modulus into one process.

The system and method allow a compaction machine operator to get an accurate indication of the compaction response of one or more materials being compacted. Specifically, the operator may be able to accurately determine when the work material has been compacted to a required threshold. Additionally, since the modulus of resilience has engineering units, it allows for a broader range of applications, including, but not limited to, the use by design engineers for building and development (e.g. roads, buildings, etc.). As design guides may use of a modulus of resilience as a primary input parameter when characterizing stiffness of work material, engineers may utilize this compaction method to ensure compliance with specification requirements.

While the disclosure is described herein using a limited number of embodiments, these specific embodiments are not intended to limit the scope of the disclosure as otherwise described and claimed herein. Modification and variations from the described embodiments exist. More specifically, the following examples are given as a specific illustration of embodiments of the claimed disclosure. It should be understood that the invention is not limited to the specific details set forth in the examples.

We claim:

1. A method for determining a modulus of resilience of a work material being compacted by a compactor system having a roller drum, the method comprising:
   compacting the work material with the roller drum;
   sensing or calculating a contact force applied on the work material by the roller drum with at least one sensor and/or a processor;
   sensing or calculating a vertical displacement of the roller drum with the at least one sensor and/or the processor;
   calculating a work material stiffness with the processor based on the contact force and the vertical displacement; and
   determining the modulus of resilience of the work material with the processor based on a relationship between the work material stiffness and the modulus of resilience of the work material,
   wherein the relationship between the work material stiffness and the modulus of resilience includes a ratio of transverse and axial strain of the work material.

2. The method of claim 1, wherein calculating the work material stiffness further comprises determining a maximum and a minimum roller drum ground contact force.

3. The method of claim 1, wherein calculating the work material stiffness further comprises determining a maximum and a minimum vertical roller drum displacement.

4. The method of claim 1, wherein the at least one sensor is an accelerometer that senses a vertical acceleration of the roller drum.

5. The method of claim 1, further comprising sending a signal by the processor to a display indicating whether the modulus of resilience of the work material has met a predetermined threshold.

6. The method of claim 1, wherein determining the modulus of resilience results in a force per area value.

7. The method of claim 1, wherein the relationship between the work material stiffness and the modulus of resilience includes at least one physical property of the roller drum.

8. The method of claim 1, wherein determining the modulus of resilience further comprises using an iterative method.

9. A compactor system for determining a modulus of resilience of a work material during a compaction operation, the compactor system comprising:
   at least one roller drum configured to compact the work material;
   at least one sensor configured to sense at least one of a vertical acceleration, a vertical displacement, and a force of a compactor system component; and
   a processor configured to
   calculate a contact force at an interface between the at least one roller drum and the work material in response to the at least one sensor, calculate a displacement of the at least one roller drum in response to the at least one sensor, calculate a stiffness of the work material based on the contact force and the displacement, and determine the modulus of resilience of the work material based on a relationship between the stiffness of the work material and the modulus of resilience of the work material, wherein the relationship between the work material stiffness and the modulus of resilience includes a ratio of transverse and axial strain of the work material.

10. The compactor system of claim 9, wherein the processor is further configured to send a signal to a display indicating whether the modulus of resilience of the work material has met a predetermined threshold.

11. The compactor system of claim 9, wherein the relationship between the work material stiffness and the modulus of resilience includes at least one physical property of the roller drum.

12. The compactor system of claim 9, wherein the processor is further configured to use an iterative method to determine the modulus of resilience.

13. A compactor system for determining a modulus of resilience of a work material during a compaction operation, the compactor system comprising a processor configured to determine a work material stiffness based on a force applied to the work material by the compactor system and a vertical displacement of the compactor system, determine the modulus of resilience of the work material based on a relationship between the work material stiffness and the modulus of resilience of the work material, and employ an iterative method to determine the modulus of resilience.

14. The compactor system of claim 13, wherein the processor is further configured to send a signal to a display indicating whether the modulus of resilience of the work material has met a predetermined threshold.

15. The compactor system of claim 13, wherein the relationship between the work material stiffness and the modulus of resilience includes a ratio of transverse and axial strain of the work material.

16. The compactor system of claim 13, further comprising at least one roller drum.

17. The compactor system of claim 16, wherein the relationship between the work material stiffness and the modulus of resilience includes at least one physical property of the at least one roller drum.

* * * * *